(12) United States Patent
Ruff

(10) Patent No.: US 10,624,944 B2
(45) Date of Patent: Apr. 21, 2020

(54) ANTI-INFLAMMATORY PEPTIDES FOR TREATING NON-ALCOHOLIC STEATOHEPATITIS (NASH)

(71) Applicant: Creative Bio-Peptides Inc., Potomac, MD (US)

(72) Inventor: Michael R. Ruff, Potomac, MD (US)

(73) Assignee: Creative Bio-Peptides Inc., Potomac, MD (US)

(*) Notice: Subject to any disclaimer, the term of this patent is extended or adjusted under 35 U.S.C. 154(b) by 0 days.

(21) Appl. No.: 16/010,847

(22) Filed: Jun. 18, 2018

(65) Prior Publication Data
US 2018/0360907 A1 Dec. 20, 2018

Related U.S. Application Data

(60) Provisional application No. 62/521,935, filed on Jun. 19, 2017.

(51) Int. Cl.
*A61K 38/08* (2019.01)
*A61K 38/00* (2006.01)
*A61P 1/16* (2006.01)
*C07K 7/06* (2006.01)
*C07K 7/00* (2006.01)

(52) U.S. Cl.
CPC ............. *A61K 38/08* (2013.01); *A61P 1/16* (2018.01)

(58) Field of Classification Search
CPC ........... A61K 38/08; A61K 38/00; A61P 1/16; C07K 7/06; C07K 7/00
USPC .................................. 514/21.8, 1.1; 530/300
See application file for complete search history.

(56) References Cited

U.S. PATENT DOCUMENTS

| 5,529,983 | A | * | 6/1996 | Pert | ............. | C07K 14/005 |
|---|---|---|---|---|---|---|
| | | | | | | 514/13.1 |
| 6,242,564 | B1 | * | 6/2001 | Pert | ............. | A61K 38/162 |
| | | | | | | 530/328 |
| 2019/0022166 | A1 | * | 1/2019 | Ruff | ............. | A61K 38/08 |

* cited by examiner

*Primary Examiner* — Julie Ha
(74) *Attorney, Agent, or Firm* — Scott Houtteman; Houtteman Law LLC

(57) ABSTRACT

A method of treating liver inflammation in an individual caused by excess fat deposition, sometimes called "fatty liver disease", which may be caused by metabolic syndrome, insulin resistance, or gut microbial dysbiosis, and which may lead to the serious and potentially life-threatening condition of non-alcoholic steatohepatitis (NASH). A composition composed of an all-D amino acid peptide and a pharmaceutically acceptable carrier is prepared and administered to a patient. The D peptide has the general structure: A-B-C-D-E in which
  A is Ser, Thr, Asn, Glu, Ile.
  B is Ser, Thr, Asp, Asn,
  C is Thr, Ser, Asn, Arg, Lys, Trp,
  D is Tyr, and
  E is Thr, Ser, Arg, Gly.
The composition acts to suppress inflammation underlying steatohepatitis. The D peptide may be esterified, glycosylated, or amidated at E to enhance tissue distribution by promoting egress from the circulation and penetration into the liver.

5 Claims, 4 Drawing Sheets
Specification includes a Sequence Listing.

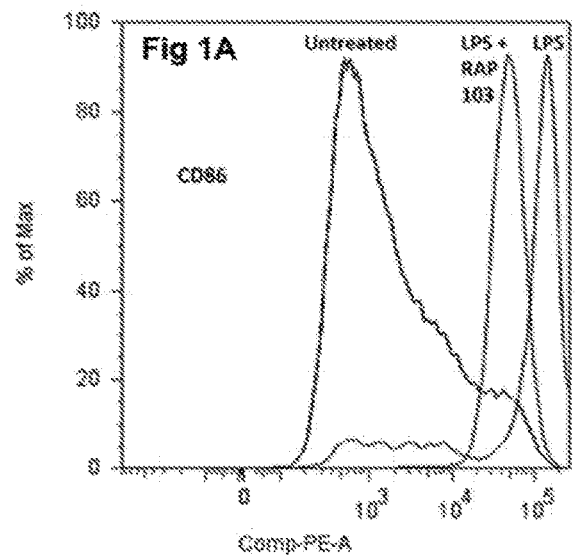
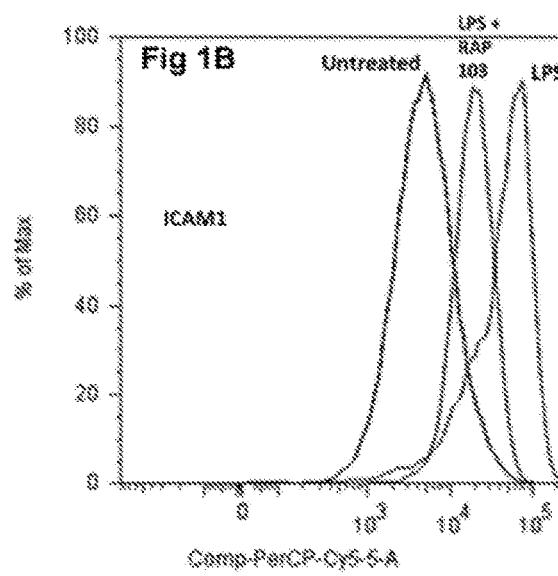
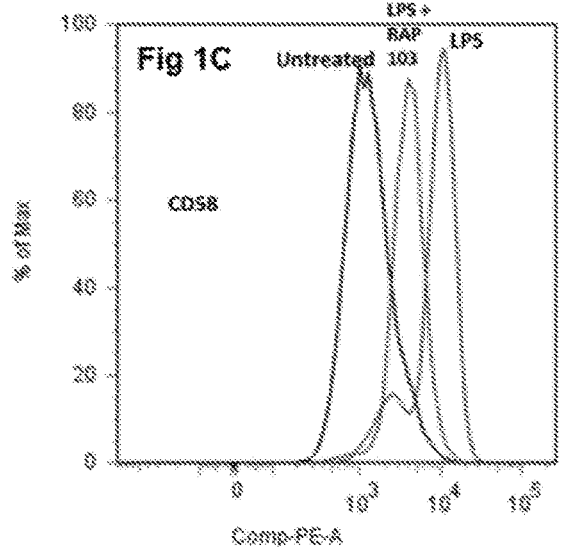
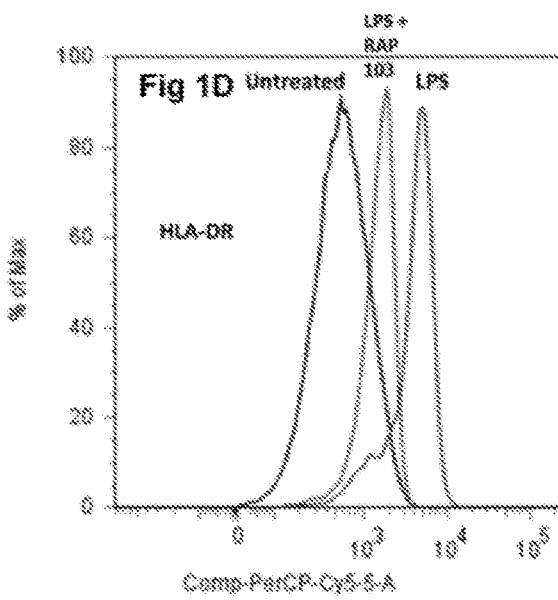

SEQUENCE LISTING

```
<160> NUMBER OF SEQ ID NOS: 14

<210> SEQ ID NO 1
<211> LENGTH: 5
<212> TYPE: PRT
<213> ORGANISM: Human immunodeficiency virus

<400> SEQUENCE: 1

Thr Thr Asn Tyr Thr
1               5

<210> SEQ ID NO 2
<211> LENGTH: 5
<212> TYPE: PRT
<213> ORGANISM: Human immunodeficiency virus

<400> SEQUENCE: 2

Ser Ser Thr Tyr Arg
1               5

<210> SEQ ID NO 3
<211> LENGTH: 5
<212> TYPE: PRT
<213> ORGANISM: Human immunodeficiency virus

<400> SEQUENCE: 3

Ser Thr Asn Tyr Thr
1               5

<210> SEQ ID NO 4
<211> LENGTH: 5
<212> TYPE: PRT
<213> ORGANISM: Human immunodeficiency virus

<400> SEQUENCE: 4
```

Thr Thr Ser Tyr Thr
1               5

<210> SEQ ID NO 5
<211> LENGTH: 5
<212> TYPE: PRT
<213> ORGANISM: Human immunodeficiency virus

<400> SEQUENCE: 5

Asn Thr Ser Tyr Gly
1               5

<210> SEQ ID NO 6
<211> LENGTH: 5
<212> TYPE: PRT
<213> ORGANISM: Human immunodeficiency virus

<400> SEQUENCE: 6

Glu Thr Trp Tyr Ser
1               5

<210> SEQ ID NO 7
<211> LENGTH: 5
<212> TYPE: PRT
<213> ORGANISM: Human immunodeficiency virus

<400> SEQUENCE: 7

Asn Thr Ser Tyr Arg
1               5

<210> SEQ ID NO 8
<211> LENGTH: 5
<212> TYPE: PRT
<213> ORGANISM: Human immunodeficiency virus

<400> SEQUENCE: 8

Ile Asn Asn Tyr Thr
1               5

<210> SEQ ID NO 9
<211> LENGTH: 5
<212> TYPE: PRT
<213> ORGANISM: Human immunodeficiency virus

<400> SEQUENCE: 9

Ile Asp Asn Tyr Thr
1               5

<210> SEQ ID NO 10
<211> LENGTH: 5
<212> TYPE: PRT
<213> ORGANISM: Human immunodeficiency virus

<400> SEQUENCE: 10

Thr Asp Asn Tyr Thr
1               5

<210> SEQ ID NO 11
<211> LENGTH: 5
<212> TYPE: PRT
<213> ORGANISM: Human immunodeficiency virus

<400> SEQUENCE: 11

Thr Asp Ser Tyr Ser
1               5

```
<210> SEQ ID NO 12
<211> LENGTH: 5
<212> TYPE: PRT
<213> ORGANISM: Human immunodeficiency virus

<400> SEQUENCE: 12

Thr Asn Ser Tyr Arg
1               5

<210> SEQ ID NO 13
<211> LENGTH: 5
<212> TYPE: PRT
<213> ORGANISM: Human immunodeficiency virus

<400> SEQUENCE: 13

Asn Thr Arg Tyr Arg
1               5

<210> SEQ ID NO 14
<211> LENGTH: 8
<212> TYPE: PRT
<213> ORGANISM: Human immunodeficiency virus

<400> SEQUENCE: 14

Ala Ser Thr Thr Thr Asn Tyr Thr
1               5
```

ANTI-INFLAMMATORY PEPTIDES FOR TREATING NON-ALCOHOLIC STEATOHEPATITIS (NASH)

This application claims the benefit of U.S. Provisional Application Ser. No. 62/521,935, filed Jun. 19, 2017.

FIELD OF THE INVENTION

The present invention relates broadly to excess fat deposits resulting from diet, obesity, metabolic syndrome, insulin resistance or gut microbiota and therapeutic small peptides to treat the serious and potentially life-threatening conditions of type 2 diabetes, chronic kidney disease, heart failure and particularly the liver inflammation caused by non-alcoholic steatohepatitis (NASH).

BRIEF DESCRIPTION OF THE DRAWINGS

FIGS. 1A-D illustrate that all-D-TTNYT (SEQ ID NO:1) blocks TLR4-mediated maturation of antigen presenting dendritic cells.

INTRODUCTION

Figure 2:
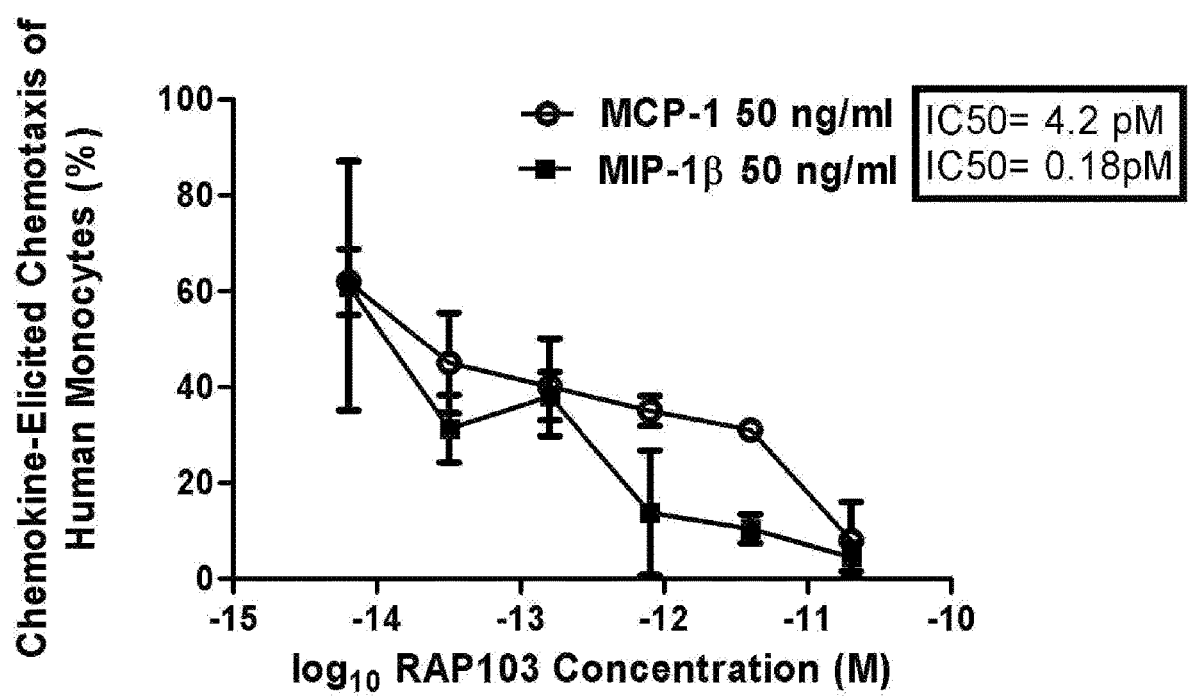
FIG. 2 Illustrates all-D-TTNYT (SEQ ID NO:1) potently blocking both MCP-1 (CCL2) and MIP-1β (CCL4)-elicited chemotaxis of human monocytes at CCR2 and CCR5 receptors, respectively.

Non-alcoholic fatty liver disease (NAFLD) is the most common liver disease in developed countries, and is strongly associated with obesity, Type II diabetes or insulin resistance, hypertension, and dyslipidemia and has been regarded as the liver manifestation of the metabolic syndrome (MS). The composition of the gut microbiota has been shown to differ in lean and obese humans and animals and to change rapidly in response to dietary factors. The gut microbiota may also influence the development of conditions characterized by low-level inflammation, such as MS, obesity and type 2 diabetes, through systemic exposure to bacterial lipopolysaccharide derived from the intestinal microbiota. Such systemic inflammation promotes steatohepatitis.

NAFLD is characterized by an accumulation of fat (lipid droplets), and is present in up to one-third of the general population while 75% of obese individuals have hepatic steatosis. NAFLD is associated with the development of cardiovascular disease (CVD) since the severity of liver histology in NAFLD patients is closely associated with markers of early atherosclerosis and independently predicts the risk of future CVD events. NAFLD therefore seems to be an early mediator of atherosclerosis and treatments for hepatic steatosis may reduce CVD events.

Non-alcoholic steatohepatitis (NASH) is a more severe form of NAFLD with inflammation and degeneration of hepatocytes as a result of excessive fat in the liver. The prevalence of NASH is 2-6% in the general population, with some estimates as high as 12%. For the diabetic population, the number rises to 22%. Up to 20% of adults with NASH develop cirrhosis and up to 11% may experience liver-related deaths. Cirrhosis is a serious condition which increases the risk of subsequent progression to hepatocellular carcinoma (HCC), the fifth most common tumor worldwide, and the third leading cause of cancer-related death.

There are numerous risk factors and predictors of NASH including age, obesity and Body Mass Index (BMI), insulin sensitivity, dyslipidemia, hypertension and increase of liver enzymes. Patients with NASH have increased risk for myocardial infarction, stroke and peripheral vascular disease.

Reducing the fat in the liver that drives inflammation and fibrosis is of paramount importance, but the inability to lose weight is a hallmark of metabolic syndrome and insulin resistance and is not in itself typically successful and therefore not sufficient to overcome the risk of NASH. There are no medicines that have been approved to treat NAFLD and NASH and the compounds of this invention can provide for an unmet medical need.

DETAILED DESCRIPTION

The present invention relates to compositions and a method for modulating, in particular reducing, an excessive immune response in an animal, such as a human or another mammal, specifically in the liver due to excess fat accumulation which may lead to fibrosis, hepatitis, loss of liver function, and death.

In one embodiment, the invention relates to compositions and a method for modulating, and in particular reducing, the inflammatory reaction in the liver of individuals who experience NAFLD, NASH.

NASH may reflect a disease where inflammation is followed by steatosis. Therefore, in order to reduce the deleterious effects of steatosis and halt the development of fibrosis and hepatitis, as well as the cardiovascular and hepatocellular carcinoma risks associated with NAFLD and its more severe form NASH, a drug candidate should confer anti-inflammatory properties. These properties would also be beneficial in viral infections of the liver, an example being hepatitis B, or alcoholic liver disease, a manifestation of alcohol overconsumption, which also includes fatty liver (steatosis) with inflammation causing chronic hepatitis with liver fibrosis or cirrhosis.

Obesity is associated with chronic low-grade inflammation perpetuated by visceral adipose with overproduction of proinflammatory molecules. Morbidly obese patients with NAFLD were studied for 84 genes encoding inflammatory cytokines, chemokines, their receptors, and other components of an inflammatory response. The mRNA levels of interleukin 8 (IL8), chemokine CCL4 (MIP-1β), and its receptor chemokine receptor type 5 (CCR5) showed a significant increase in patients with advanced hepatic inflammation and were correlated with the severity of the hepatic inflammation (1).

NAFLD has further been considered to be under the influence of the gut microbiota, which might exert inflammatory effects on the human host after intestinal absorption and delivery to the liver via the portal vein. TNFα, IL-6 and IFNγ were detected in an NAFLD group compared to healthy controls (2). Gut microbiota-mediated inflammation of the intestinal mucosa therefore seems to play an important role in the pathogenesis of NAFLD which the subject inventive peptides can treat. Benefits of the subject peptides in suppressing intestinal production of inflammatory cytokines and chemokines resulting from gut microbial dysbiosis or metabolic syndrome would extend to other conditions with an inflammatory pathogenesis, including diabetic neuropathy, cardiovascular diseases and neurodegenerative conditions like Alzheimer's Disease and traumatic brain injury.

Gut-derived bacterial endotoxins, such as lipopolysaccharide (LPS), contribute to the pathogenesis of steatosis and steatohepatitis by activating Kupffer cells, the resident liver macrophages. LPS stimulated production of IL-6, via activation of its downstream effector signal transducer and activator of transcription (STAT) 3 is reported to drive hepatic lipid storage. Thus TLR4/MyD88 activation by LPS, as well as IL-6 are therapeutic targets in endotoxemia and NASH which the subject inventive peptides block.

Further support for chemokine receptor targets in NAFLD comes from studies that show CCR2 and CCR5 and their ligands, including CCL2 (MCP-1) and CCL5 (RANTES), are reported to mediate liver fibrogenesis by promoting monocyte/macrophage recruitment and tissue infiltration, as well as hepatic stellate cell activation. A dual CCR2/CCR5 antagonist significantly reduced the non-alcoholic fatty liver disease activity score in an animal model of NASH as a result of its anti-inflammatory activities (3).

A role for CCR5 in development of hepatic steatosis in a high fat diet mouse model of NAFLD has been shown for the CCR5 antagonist "Maraviroc", first developed as an inhibitor of CCR5-tropic HIV viruses. Maraviroc ameliorated hepatic steatosis while CCL5/RANTES expression was also significantly lower with maraviroc treatment (4).

More specifically, an embodiment of the invention relates to compositions and a method for modulating, and in particular reducing, the secretion of the inflammatory cytokines IL-1, IL-6, IL-8, IL-12, IL-23 and TNFα, chemokine ligands including CCL2, CCL3, and CCL5, and their receptors CCR2 and CCR5, or by blocking chemokine induced migration of monocytes or T cells into fatty liver, their adherence and localization in liver to ICAM-1 receptors and therefore broadly blocking degeneration of hepatocytes as a result of excessive fat and inflammation in the liver.

Dala1-peptide T-amide (DAPTA) is derived from the HIV envelope protein (5) and is an antagonist of CCR5 (6) and CCR2 (7) which blocks monocyte infiltration into injured brain or spinal cord and lowers expression of inflammatory cytokines such as TNFα, Il-1, IL-6, and IL-8 in animals and people (7-9) as well as IL-12p40 a component of the heterodimeric cytokine IL-23, which has been implicated as key target in immune-mediated inflammatory diseases like psoriasis, which DAPTA improves, and Crohn's Disease. DAPTA, and improved analogs that share the same biological effects will be useful in treating NAFLD, NASH and these other conditions.

The anti-inflammatory effects of DAPTA are retained in the C-terminal five amino peptide TTNYT (SEQ ID NO:1), and analogs can be created which can be made orally active when the amino acids are in the all-D form (7). Other modifications such as charge "cationization" provide further improvements in tissue delivery and distribution.

Because DAPTA and all-D-TTNYT (SEQ ID NO:1) (generic name RAP103) block the actions of several inflammatory receptors and are multi (CCR2/CCR5) chemokine receptor antagonists, they provide broader receptor antagonism to inhibit multiple innate immune pathways. These distinguishing features may afford more effective "coverage" of the pharmacological receptor cluster that mediates liver inflammation and causes NASH and so deliver a beneficial therapeutic outcome to block development of the NAFLD/NASH inflammatory cascade.

All compounds disclosed in these specifications are useful for the present invention. The compounds block multiple chemokine receptors and cytokines implicated in the discussed steatohepatitis syndromes (NAFLD/NASH).

The lead compound DAPTA was derived from the HIV gp120 octapeptide Ala-Ser-Thr-Thr-Thr-Asn-Tyr-Tyr (SEQ ID NO:14). This all-L amino acid octapeptide was called Peptide T because 50% of the amino acid residues are threonines (Thr). This peptide has been identified from the human immune deficiency virus (HIV) external glycoprotein molecule gp120, specifically near the bridging sheet of the V2 loop, a region which is responsible for virus binding via the CCR5 and related chemokine receptors, such as CCR2, CCR8, CX3CR1. All these chemokine receptors function as HIV entry receptors and are targets of the subject inventive peptides. The peptides of the invention we here describe are antagonists of multiple HIV entry chemokine receptors which have been shown to mediate NASH pathologies, such as CCR2 and CCR5. Further modifications of Peptide T and DAPTA have been created in the example (SEQ ID NO: 1) all-D-TTNYT (SEQ ID NO:1) (generic name RAP103) that confers the improvements of oral bioavailability and enhanced tissue distribution.

Peptides of the present invention represent a pentapeptide minimal bioactive sequence of the octapeptide Peptide T (ASTTTNYT, (SEQ ID NO:14)), and its human use analog "DAPTA", Dala1-peptide T-amide, first described as an antiviral agent by Pert, et al. (U.S. Pat. No. 5,276,016). The modified peptides of the invention have multiple desired features that yield in vivo efficacy including potency and receptor-selectivity, delivery to target tissue, and stability to multiple degradative proteases, all of which provide a beneficial therapeutic preparation for the subject use in liver inflammation, steatohepatitis, NAFLD and NASH.

Method to Create Oral Bioavailibility

Practitioners skilled in the art of peptide design understand that it is overwhelmingly the case that modifications of the peptide backbone, including substitution of D-amino acids, particularly at receptor-active sites in the peptide, cause loss of activity, and in some modifications complete inactivity. In fact, the use of D-amino acid substitutions is commonly used to identify, by loss of function, critical pharmacophore residues in a peptide.

Thus, an unexpected and non-obvious aspect of the present invention is the use of all-D amino-acids in the creation of the orally bioactive peptides that target chiral molecules, such as cell surface GPCR receptors. A recent review (10) of oral delivery of therapeutic proteins and peptides indicates that "Despite extensive research efforts, oral delivery of a therapeutic peptide or protein is still a challenge for pharmaceutical industries and researchers. Therefore, because of the short circulatory half-life exhibited by peptides in vivo, they need to be administered frequently resulting in increased cost of treatment and low patient compliance" and in many cases oral delivery is not even possible. Generally, protein and peptide drugs are rapidly denatured or degraded by the low pH environment of the gastric media or the hydrolytic enzymes in the gastrointestinal tract.

Chiral selectivity of ligand action is not surprising and is well understood as a principal of enzymology. For example, a chiral specificity is noted in majority of the NSAIDs (non-steroidal anti-inflammatory drugs). For NSAIDs the enantiomer with S configuration almost exclusively possesses the ability to inhibit prostaglandin activity. R-enantiomers of NSAIDs have poor COX inhibitory activity (11). The opiate receptor is an example of a G-protein coupled receptor showing ligand stereoselectivity, in which levorphanol is the active analgesic component of the racemic mixture racemorphan, while its stereoisomer dextrorphan, is inactive.

Some examples of all-D-peptide activity exist, such as the anti-microbial human θ-defensins, which are cationic peptides which disrupt bacterial, but not mammalian, cell membranes. There is no stereo-selective biological interaction of a cationic peptide to a membrane. Defensin activity is derived from a charge disruption of a membrane. This is different from the action of the present inventive peptides which target stereo-specific cell surface receptors and are highly sensitive to ligand conformation and shape.

Figure 3:
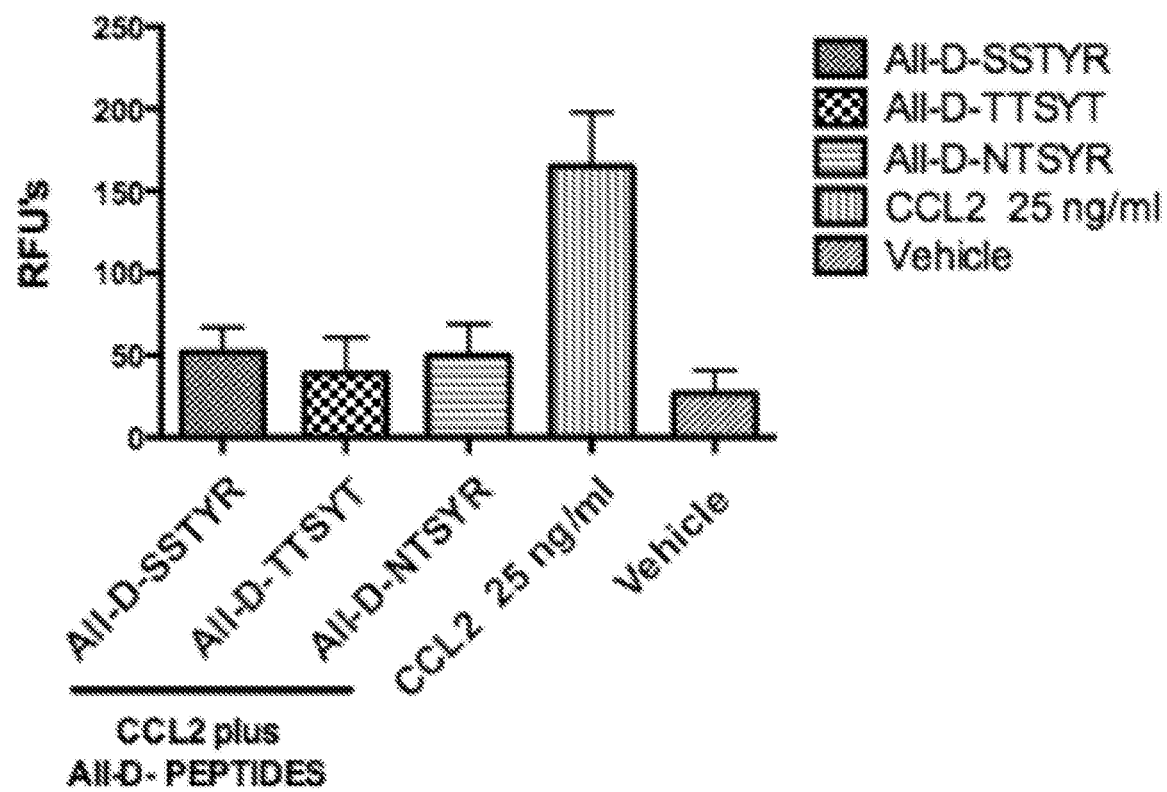
FIG. 3 Illustrates the effects of three additional all-D amino acid peptides in blocking CCL2 (MCP-1) chemotaxis at low concentration.
Figure 4A:
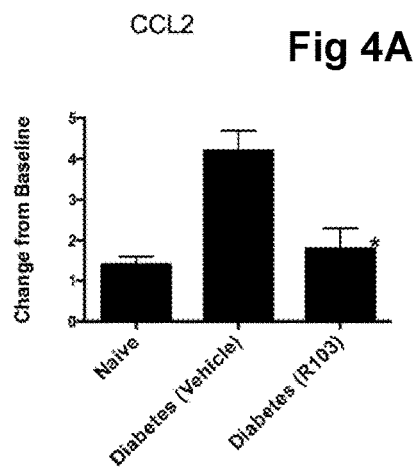
FIGS. 4A-F illustrate all-D-pentapeptide TTNYT (SEQ ID NO:1) lowering expression of chemokines CCL2 and CCL3, chemokine receptors CCR2 and CCR5, and cytokines IL-1 and TNFα in rats.
Figure 4B:
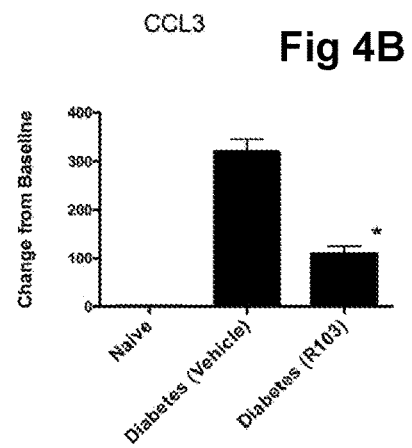
Figure 4C:
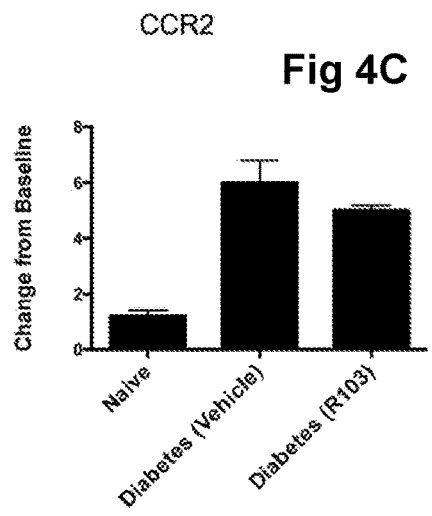
Figure 4D:
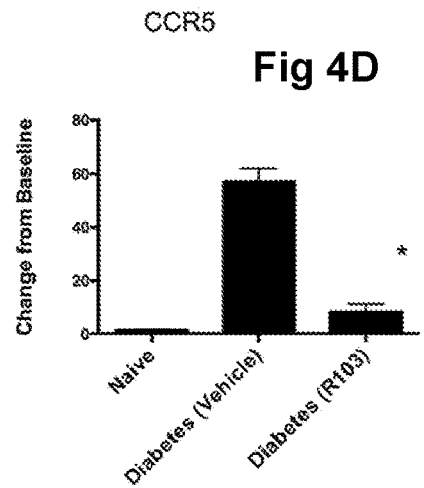
Figure 4E:
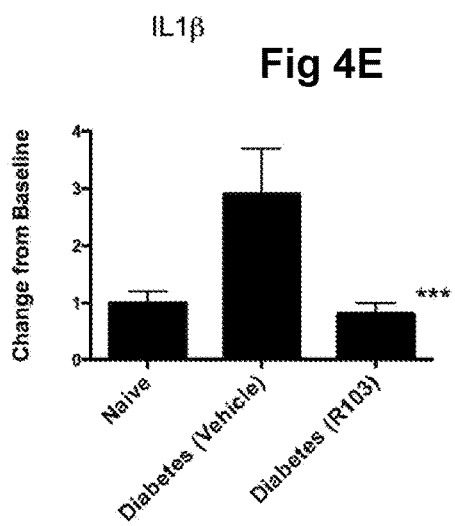
Figure 4F:
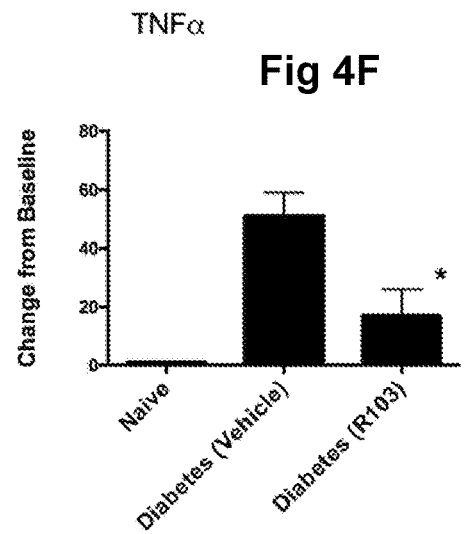

The bioactivity of a receptor active all-D peptide is an unexpected and non-obvious aspect of the present invention in view of an earlier study, Pert (5), FIGS. 3 and 4, and the related U.S. Pat. No. 5,276,016 which showed that that D for L substitutions in linear peptide ASTTTNYT (SEQ ID NO:14) can cause great loss of potency.

Having one D substitution in DAPTA, in the specific position No1, (the D-ala) retains receptor potency, primarily as this residue of the peptide is not needed for bioactivity, indeed may be completely removed. The terminal pentapeptide however is responsible for the biopotency, and D amino acid modifications of these residues are not well tolerated.

Thus, making an additional D substitution in DAPTA, in the terminal pentapeptide required for activity, at position No 8 (the D-Thr), results in loss of 99 to 99.9% of the activity. It is therefore shown that introduction of L to D substitutions cannot be made in a general fashion, and that these modifications can, and typically do, destroy biopotency by disrupting the peptide structure required for receptor potency.

This point is further made in Brenneman, 1988 (12), with specific reference to the peptide TTNYT (SEQ ID NO:1). See FIG. 2 and Table 1. Upon making the L to D substitution in position 4 (Tyr), the peptide completely loses activity.

A detailed study of the peptide TTNYT (SEQ ID NO:1) and L to D substitutions was published in
Smith, 1988 (13), Refer to FIG. 3. Introduction of single L to D substitutions in each position 1, 2, 3, 4, results in loss of potency, and all of the D-amino acid substitutions are substantially less active (50x) to completely inactive.

As such the use of D-substitutions by Andersen (U.S. Pat. Nos. 6,011,014 or 6,265,374) in "each" position of DAPTA has not been reduced to practice. The published data shows that in no instance does a D for L amino-acid substitution in the core C-terminal pentapeptide of DAPTA achieve comparable potency to the all-L form, rather D substitutions result in loss of activity, sometimes complete loss of biopotency in a position dependent fashion.

The notion that an all-D peptide would retain significant potency is furthermore novel in consideration of long accepted art of Stewart and Woolley (14) who prepared all-D peptides of a hormone. For example, from their article, "In contrast to the change of a single residue, the inversion of all the amino-acid residues in a pentapeptide which has hormonal activity of MSH was found to cause loss of hormonal activity . . . ."

Further in this paper the authors write "because there is as yet no general method
for predicting the structural requirements required to make antimetabolites of peptides, we synthesized all-D bradykinin (note 9 amino acids, similar size to the 8-amino acid Formula 1 peptide of Andersen) in an effort to find out whether inversion of all the amino-acids of a peptide may be a generally applicable method for synthesis of peptide antagonists."

The authors then concluded: "Amounts of all-D-bradykinin up to 50,000 times the
the standard challenge of bradykinin showed neither any inhibition of the response to bradykinin, or any bradykinin-like effect. It would thus seem that inversion of all the amino-acid residues may not be a generally applicable method for formation of antimetabolites of biologically active peptides".

Michaelis and Trigg (U.S. Pat. No. 5,798,335) have claimed modified analogs of DAPTA that incorporated D-amino acids. Andersen et al (U.S. Pat. Nos. 6,011,014 and 6,265,374) also claim a treatment of inflammation and multiple sclerosis using DAPTA and modified analogs of DAPTA that incorporated D-amino acids. No reduction to practice for any all-D-amino acid modified peptide was provided, and no example of claimed benefit or treatment use with an all-D-amino acid pentapeptide was provided. No all-D-peptide of SEQ ID NO: 1-13 of the present invention was claimed in these prior applications.

The ability to make D for L amino acid substitutions in all positions however creates the possibility to make orally stable peptide compounds. Stability of peptides in target tissues due to digestive enzymes has limited their broad utility. The ability to create all-D peptides that retain potency is an unexpected general method of creating peptides SEQ ID NO: 1-13, and possibly others, which may be stabilized to proteolysis, while retaining biopotency, so these peptides benefit from enhanced stability.

Oral delivery solves another problem that is common with peptides, their propensity to aggregate in liquid solutions and lose biopotency, as the peptides may be compounded in solid forms, such as oral pills, with long shelf lives.

Thus, neither Pert et al. (U.S. Pat. No. 5,276,016), who first used D-amino acids in the octapeptide Peptide T (ASTTTNYT (SEQ ID NO:14)) to create the analog DAPTA (Dala$^1$-peptide T-amide), or Michaelis and Trigg (U.S. Pat. No. 5,798,335), or Andersen et al (U.S. Pat. Nos. 6,011,014 and 6,265,374) teach substitution of all the naturally occurring L-amino acids by D-amino acids in Peptide T or DAPTA.

The use of D-substitutions in "each" position claimed by Michaelis and Trigg or Andersen et al., cannot be inferred to mean in "all" positions, and in any event, has not been reduced to practice in these inventions. The data of Brennemen, 1998 (12) and Smith, 1988 (13) shows that in no instance does a D for L amino-acid substitution in Sequence ID 1 achieve comparable potency to the all-L form, rather D substitutions result in loss of activity, sometimes complete loss of biopotency in a position dependent fashion.

Therefore, it cannot be claimed that making all of the amino acids into D-form is obvious. The specific facts relating to the peptides of this invention from the prior published art inform the exact opposite view, that making an all-D peptide would not be efficacious as an anti-inflammatory agent that targets innate immune system G-protein coupled receptors, such as the chemokine receptors.

This type of structure-function analysis is a key to drug design and must be determined experimentally in each instance. Our recognition that a pentapeptide fragment of DAPTA (Sequence ID 1) comprised of all-D-amino acids retained substantial potency led us to determine that other peptapeptides retained activity as all-D-amino acid forms in specific chemokine receptor functional tests.

The use of all-D-amino acids containing peptides related to SEQ ID NO: 1 that retained substantial biopotency to block CCR5 receptors was first disclosed in U.S. Ser. No. 12/688,862, however no oral use was enabled or claimed, nor have any prior disclosures including U.S. application Ser. No. 13/024,324 identified uses to treat steatohepatic liver diseases like NASH, or hepatic inflammation in general, from any cause.

A peptide of the present invention (all-D-TTNYT (SEQ ID NO:1)) has previously been proposed to be effective in modulating inflammation caused by CCR5 receptors (application Ser. No. 12/688,862, US 2010/0184705 A1). A further use in reducing pain in peripheral neuropathy (Ser. No. 13/024,324), by targeting CCR5, CCR2 and CX3CR1 chemokine receptors, has been disclosed. Neither of these applications teaches a use in NAFLD or NASH. A prior U.S. Pat. No. 5,248,667 teaches a method of treating psoriasis by use of the peptide "DAPTA" and related D-peptides.

By the multiple improvements disclosed in this invention, specifically: 1) achieving oral bioavailability by use of the all-D amino acid modifications that unexpectedly retain receptor biopotency for these peptides, 2) reduced size compared to DAPTA (pentapeptide compared to an octapeptide) to facilitate entry into tissues, and in some uses 3) "cationization" of the peptide so that the C-terminal carboxylic acid may be esterified, glycosylated, or amidated to further enhance tissue distribution, a peptide may be administered to individuals seeking modification of inflammation such as in NASH, the subject invention creates an efficacious composition that provides the desired treatment benefits.

Other Active Compounds

Applicant believes other pentapeptides comprised of all-D-amino acids will be effective, including the peptides: SSTYR (SEQ ID NO:2), STNYT (SEQ ID NO:3), TTSYT (SEQ ID NO:4), NTSYG (SEQ ID NO:5), ETWYS (SEQ ID NO:6), NTSYR (SEQ ID NO:7), INNYT (SEQ ID NO:8), IDNYT (SEQ ID NO:9), TDNYT (SEQ ID NO:10), TDSYS (SEQ ID NO:11), TNSYR (SEQ ID NO:12) and NTRYR (SEQ ID NO:13), as well as the octapeptide ASTTTNYT (SEQ ID NO:14).

According to a first aspect of the present invention, there is provided the use of a linear peptide of SEQ ID NO: 1 wherein all amino acids are in the D-stereoisomeric configuration:
Sequence ID 1: A-B-C-D-E wherein:
A is Ser, Thr, Asn, Glu, Arg, Ile, Leu,
B is Ser, Thr, Asp, Asn,
C is Thr, Ser, Asn, Arg, Gln, Lys, Trp,
D is Tyr, and
E His Thr, Ser, Arg, Gly.

Candidates for E may be esterified, glycosylated, or amidated.

The modifications of E (esterified, glycosylated, or amidated) enhance delivery to target tissues by charge cationization of the peptide at physiological pH in the range of 6 to 8. Previously the terminal amide modification was introduced by Pert et al. (U.S. Pat. No. 5,276,016) to provide protection from carboxypeptidase degradation of DAPTA, and others, including Michaelis and Trigg or Andersen et al., have employed this rationale. That is not the function here, as SEQ ID NO:14, is fully protected to degradation and needs no terminal amide (—NH$_2$), ester, or glycosyl moiety to block proteases.

We have assessed that a terminal amide (—NH$_2$) modification in the all-D-peptides of the subject invention enhances its transition across biological membranes and promotes entry into target tissues by charge cationization. Such modification can be achieved by general methods (ester, or glycosyl etc.) to modify the terminal carboxylic moiety, which at physiological pH would have a negative charge. Therefore, such modification provides an additional and novel improvement to the specific peptides of this invention by enhancing their egress from the circulation and delivery to target issues.

The peptides or peptide formulations may be used alone or in combination with any other pharmaceutically active compound or an excipient to treat the inflammation of NASH.

The peptides may be administered orally, bucally, parenterally, topically, rectally, vaginally, by intranasal inhalation spray, by intrapulmonary inhalation or in other ways. In particular, the peptides according to the invention may be formulated as pills for oral administration, in controlled release formulations, for injection (for example subcutaneous, intramuscular, intravenous, intra-articular or intra-cisternal injection), for infusion, and may be presented in unit dose form in ampoules or tablets or in multidose vials or other containers with an added preservative. The compositions may take such forms as suspensions, solutions, or emulsions or gels, and may contain formulatory agents such as suspending, stabilizing and/or dispersing agents. Alternatively, the active ingredient may be in powder and/or lyophilized form for direct administration or for constitution with a suitable vehicle (e.g. sterile, pyrogen-free water, normal saline or 5% dextrose) before use. The pharmaceutical compositions containing peptides(s) may also contain other active ingredients such as antimicrobial agents, or preservatives. The compositions may contain from 0.001-99% (w/v or, preferably, w/w) of the active material.

The compositions are administered in therapeutically or prophylactic effective does, i.e. 0.05-1000 mg of peptide per day, in particular 5-250 mg per day. Very large doses may be used as the peptide according to the invention is non-toxic. However, normally this is not required. The dose administered daily of course depends on the degree of inflammation and inflammatory response.

For administration by injection or infusion of the compositions, the daily dosage, as employed for treatment of adults of approximately 70 kg of body weight, will often range from 2-250 mg of active material which may be administered in the form of 1 to 4 doses over each day, The invention may be useful in the prevention or treatment of illness or medical conditions, particularly those involving inflammation, such as in NASH, hepatitis due to viral, bacterial or drug-induced liver inflammation and intestinal dysbiosis, a cause of NASH and other systemic inflammatory conditions.

The Invention can be Illustrated by the Following Non-Limiting Examples

To test the hypothesis that all-D-peptides which retain receptor activity may be created, with utility in inflammatory conditions, such as may occur in liver or elsewhere in the body, we first used molecular and cellular approaches to explore the inflammatory reaction in isolated immature human monocyte derived immature dendritic cells (iDCs). DCs are derived from differentiated immature monocytes and serve as the innate and adaptive antigen presenting cells of the liver, brain, skin, and other tissues.

To determine whether all-D-TTNYT (SEQ ID NO:1) blocks maturation of antigen-presenting dendritic cells, human PBMC's were isolated from peripheral blood by Ficoll-Paque centrifugation and then monocytes were isolated by negative selection using immunobeads (Miltenyi). Human monocyte derived immature dendritic cells (iDCs) were then generated by treating monocytes with GM-CSF/IL4.

The iDCs were treated with all-D-TTNYT (SEQ ID NO:1), generic name RAP103 (7), at 10-12 M for 30 min. After 30 min LPS (100 ng/ml) was added to the cells and cells were analyzed after 48 hrs. for surface maturation markers using fluorescent labeled antibodies by flow cytometry. Shown in FIG. 1 are results of CD86, HLA-DR, CD58 (adhesion molecule) and ICAM1 (adhesion molecule) expression induced by TLR4/MyD88 activation (LPS), with and without, added all-D-TTNYT (SEQ ID NO:1). As seen in the plots FIGS. 1A-D, pretreatment of cells with all-D-TTNYT (SEQ ID NO:1) reduces expression of all the maturation markers listed in the figure. These surface molecules control T cell activation and localization in tissues. Blockade of DC maturation and activation would suppress inflammation in NASH.

Our results showed that the maturation markers CD86, HLA-DR, CD58 (adhesion molecule) and ICAM1 (adhesion molecule) when stimulated via TLR4/MyD88 activation (LPS), are reduced by pre-treatment of the cells with all-D-TTNYT (SEQ ID NO:1). Similar results were obtained using all-D-TTNYT (SEQ ID NO:1)-NH$_2$. The expression of these maturation markers is well known in mediating immune cell trafficking and immune response in the context of tissue damage, antigen recognition, hepatic inflammation, hepatic stellate cell activation, and hepatic steatosis.

All-D-TTNYT (SEQ ID NO:1) however had no effect on DC maturation of these four markers caused by the antimicrobial peptide LL37, which binds to the insulin-like growth factor 1 receptor (IGF-1R) (not shown). The action of all-D-TTNYT (SEQ ID NO:1) therefore shows specificity for TLR4/MyD88 induced maturation. In liver, TLR4 is expressed by all parenchymal and non-parenchymal cell types, and contributes to tissue damage caused by a variety of etiologies. TLR4 signaling occurs in hepatic stellate cells (HSCs), the major fibrogenic cell type in injured liver, and mediates an inflammatory phenotype leading to fibrogenesis. Inhibiting DC maturation would have benefits in septic shock or other conditions with elevated TNFα levels. We conclude that all-D-TTNYT (SEQ ID NO:1) and related analogs can have a beneficial effect in NAFLD, NASH, hepatitis or septic shock, by modulating antigen presenting cell activation in liver and other tissues, such as the brain microglia or skin Langerhans cells.

FIG. 2 shows all-D[TTNYT (SEQ ID NO:1)], generic name RAP-103, is a dual-antagonist of CCR5 and CCR2 human monocyte chemotaxis. Monocytes were treated with the indicated doses of RAP-103 for 30 min before chemotaxis against human CCL2 (MCP-1) or CCL4 (MIP-1β) (both 50 ng/mL) for 90 min. Data (chemotactic index) are presented as mean±SEM. The chemotactic index for MCP-1 without RAP-103 was 2.5-3.5 times over control, whereas for MIP-1∂℃ without RAP-103, it was approximately 2 times over control. Data are presented as mean±SEM. (*P<0.05, **P<0.01 vs RAP-103 untreated). Data are from [Padi, 2012, FIG. 1]. The result shows a further useful action of these peptides as blocking of CCR2/CCR5 is beneficial in NAFLD/NASH. Dual-chemokine CCR2/CCR5 receptor antagonists may have added therapeutic value by blocking multiple inflammatory pathways.

FIG. 3 shows three further examples of all-D-versions of DAPTA related pentapeptides, all-D-SSTYR (SEQ ID NO: 2), all-D-TTSYT (SEQ ID NO: 4), and all-D-NTSYR (SEQ ID NO: 7) are similarly antagonists of CCL2 human monocyte chemotaxis and would be expected to provide benefits in inflammatory liver diseases, such as NASH. Methods are similar to those in FIG. 2.

FIG. 4 shows reductions of chemokines CCL2 and CCL3, the chemokine receptors CCR2 and CCR5, and the cytokines IL-1 and TNFα in a rodent injury model of inflammation. The specific experimental details are provided in Padi, 2012 (7). Both Dala1-peptide T-amide and all-D-TTNYT (SEQ ID NO:1) share receptor targets, and biological effects indicating they are analogs that target the same pathological processes. All of the DAPTA related peptides that we describe are therefore expected to share the same actions, benefits, and therapeutic mechanisms, as is expected from structurally related analogs. The target biomolecules relevant to NASH and liver inflammation are summarized in Table 1.

A further action of the subject peptides relevant to protecting against inflammation in NAFLD and NASH or liver damage in general, as from viral infection, is the ability to decrease inflammatory cytokines, chemokines, and their receptors which underlie the disease processes. Here it is illustrated that Dala1-peptide T-amide (DAPTA), which has only 1 of 8 amino acids in the D-configuration, lowers inflammatory cytokine levels in humans. The effect is shared by the pentapeptide all-D-TTNYT (SEQ ID NO:1) (RAP-103) which was administered by oral gavage, (0.05-1 mg/kg) for 7 days to nerve injured rats, who also showed reductions in key biomarkers identified in NASH.

TABLE 1

Summary of Biomarker Changes for DAPTA and all-D-TTNYT (SEQ ID NO: 1)

| Biomarker | Species | Change | Compound |
| --- | --- | --- | --- |
| IL-1 | Hu | decrease | DAPTA |
| IL-6 | Hu | decrease | DAPTA |
| IL-8 | Hu | decrease | DAPTA |
| IL-23 | Hu | decrease | DAPTA |
| TNFα | Hu | decrease | DAPTA |
| ICAM-1 | Hu | decrease | DAPTA |
| STAT3 | Hu | decrease | DAPTA |
| NFkB | Hu | decrease | DAPTA |
| TLR4/MyD88 | Rat | decrease | DAPTA |
| MCP-1 (CCL2) | Rat | decrease | all-D-TTNYT (SEQ ID NO: 1) |
| MIP-1α (CCL3) | Rat | decrease | all-D-TTNYT (SEQ ID NO: 1) |
| TNFα | Rat | decrease | all-D-TTNYT (SEQ ID NO: 1) |
| CCR2 | Rat | decrease | all-D-TTNYT (SEQ ID NO: 1) |
| CCR5 | Rat | decrease | all-D-TTNYT (SEQ ID NO: 1) |
| IL-β | Rat | decrease | all-D-TTNYT (SEQ ID NO: 1) |
| IL-6 | Rat | decrease | all-D-TTNYT (SEQ ID NO: 1) |

REFERENCES

1. Mehta, R., A. Birerdinc, A. Neupane, A. Shamsaddini, A. Afendy, H. Elariny, V. Chandhoke, A. Baranova, and Z. M. Younossi. 2013. Expression of inflammation-related genes is altered in gastric tissue of patients with advanced stages of NAFLD. *Mediators Inflamm* 2013: 684237.
2. Jiang, W., N. Wu, X. Wang, Y. Chi, Y. Zhang, X. Qiu, Y. Hu, J. Li, and Y. Liu. 2015. Dysbiosis gut microbiota associated with inflammation and impaired mucosal immune function in intestine of humans with non-alcoholic fatty liver disease. *Sci Rep* 5: 8096.
3. Lefebvre, E., G. Moyle, R. Reshef, L. P. Richman, M. Thompson, F. Hong, H. L. Chou, T. Hashiguchi, C. Plato, D. Poulin, T. Richards, H. Yoneyama, H. Jenkins, G. Wolfgang, and S. L. Friedman. 2016. Antifibrotic Effects of the Dual CCR2/CCR5 Antagonist Cenicriviroc in Animal Models of Liver and Kidney Fibrosis. *PLoS One* 11: e0158156.

4. Pérez-Martínez, L., P. Pérez-Matute, J. Aguilera-Lizarraga, S. Rubio-Mediavilla, J. Narro, E. Recio, L. Ochoa-Callejero, J. A. Oteo, and J. R. Blanco. 2014. Maraviroc, a CCR5 antagonist, ameliorates the development of hepatic steatosis in a mouse model of non-alcoholic fatty liver disease (NAFLD). *J Antimicrob Chemother* 69: 1903-1910.

5. Pert, C. B., J. M. Hill, M. R. Ruff, R. M. Berman, W. G. Robey, L. O. Arthur, F. W. Ruscetti, and W. L. Farrar. 1986. Octapeptides deduced from the neuropeptide receptor-like pattern of antigen T4 in brain potently inhibit human immunodeficiency virus receptor binding and T-cell infectivity. *Proc Natl Acad Sci USA* 83: 9254-8.

6. Polianova, M. T., F. W. Ruscetti, C. B. Pert, and M. R. Ruff. 2005. Chemokine receptor-5 (CCR5) is a receptor for the HIV entry inhibitor peptide T (DAPTA). *Antiviral Res* 67: 83-92.

7. Padi, S. S., X. Q. Shi, Y. Q. Zhao, M. R. Ruff, N. Baichoo, C. B. Pert, and J. Zhang. 2012. Attenuation of rodent neuropathic pain by an orally active peptide, RAP-103, which potently blocks CCR2- and CCR5-mediated monocyte chemotaxis and inflammation. *Pain* 153: 95-106.

8. Rosi, S., C. B. Pert, M. R. Ruff, K. McGann-Gramling, and G. L. Wenk. 2005. Chemokine receptor 5 antagonist D-Ala-peptide T-amide reduces microglia and astrocyte activation within the hippocampus in a neuroinflammatory rat model of Alzheimer's disease. *Neuroscience* 134: 671-676.

9. Ruff, M. R., M. Polianova, Q. E. Yang, G. S. Leoung, F. W. Ruscetti, and C. B. Pert. 2003. Update on D-ala-peptide T-amide (DAPTA): a viral entry inhibitor that blocks CCR5 chemokine receptors. *Curr HIV Res* 1: 51-67.

10. Ensign, L. M., R. Cone, and J. Hanes. 2014. Nanoparticle-based drug delivery to the vagina: A review. *J Control Release*

11. Hayball, P. J. 1996. Chirality and nonsteroidal anti-inflammatory drugs. *Drugs* 52 Suppl 5: 47-58.

12. Brenneman, D. E., J. M. Buzy, M. R. Ruff, and C. B. Pert. 1988. Peptide T sequences prevent neuronal cell death produced by the envelope protein (gp120) of the human immunodeficiency virus. *Drug Devel Res* 15: 361-369.

13. Smith, C. C., P. L. Hallberg, P. Sacerdote, P. Williams, E. Sternberg, B. Martin, C. Pert, and M. R. Ruff. 1988. Tritiated Dala1-peptide T binding: A pharmacologic basis for the design of drugs which inhibit HIV receptor binding. *Drug Devel Res* 15: 371-379.

14. Stewart, J. M., and D. W. Woolley. 1965. All-D-bradykinin and the problem of peptide antimetabolites. *Nature* 206: 619-620.

---

What is claimed is:

1. A method of treatment for non-alcoholic fatty liver disease (NAFLD), non-alcoholic steatohepatitis (NASH) and hepatitis conditions in a person comprising the steps of:
   using a composition comprising a D peptide and a pharmaceutically acceptable carrier,
   wherein said D peptide comprises five contiguous amino acids having the general structure: A-B-C-D-E in which:
   A is Ser, Thr, Asn, Glu or Ile,
   B is Ser, Thr, Asp or Asn,
   C is Thr, Ser, Asn, Arg or Trp,
   D is Tyr, and
   E is Thr, Ser, Arg or Gly,
   and all amino acids being in the D stereoisomeric configuration,
   wherein said composition is administered to a patient in a therapeutically effective dose and said composition acts to treat NAFLD, NASH, or hepatitis conditions in the patient.

2. The method as defined in claim 1 wherein said D peptide is TTNYT (SEQ ID NO: 1).

3. The method as defined in claim 1 wherein said D peptide is at most eight (8) D amino acid residues in length and contains five contiguous D amino acid residues that have a sequence selected from the group consisting of:

Thr Thr Asn Tyr Thr, (SEQ ID NO: 1)

Ser Ser Thr Tyr Arg, (SEQ ID NO: 2)

Ser Thr Asn Tyr Thr, (SEQ ID NO: 3)

Thr Thr Ser Tyr Thr, (SEQ ID NO: 4)

Asn Thr Ser Tyr Gly, (SEQ ID NO: 5)

Glu Thr Trp Tyr Ser (SEQ ID NO: 6)

Asn Thr Ser Tyr Arg (SEQ ID NO: 7)

Ile Asn Asn Tyr Thr, (SEQ ID NO: 8)

Ile Asp Asn Tyr Thr (SEQ ID NO: 9)

Thr Asp Asn Tyr Thr (SEQ ID NO: 10)

Thr Asp Ser Tyr Ser (SEQ ID NO: 11)

Thr Asn Ser Tyr Arg (SEQ ID NO: 12)

Asn Thr Arg Tyr Arg. (SEQ ID NO: 13)

4. The method as defined in claim 1 wherein E may be esterified, glycosylated, or amidated to enhance tissue distribution.

5. The method as defined in claim 1 wherein said D peptide is Dala1-peptide T-amide (DAPTA).

* * * * *